(12) United States Patent
Quinones et al.

(10) Patent No.: US 8,365,584 B1
(45) Date of Patent: Feb. 5, 2013

(54) APPARATUS FOR INSPECTING TURBOMACHINE COMPONENTS IN-SITU

(75) Inventors: Diego Quinones, Rexford, NY (US); Daniel Lawrence Banowetz, Glenville, NY (US); Gareth William David Lewis, Lexington, MA (US); Thomas Earnest Moldenhauer, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 90 days.

(21) Appl. No.: 13/181,803

(22) Filed: Jul. 13, 2011

(51) Int. Cl.
*G01M 15/14* (2006.01)
(52) U.S. Cl. ..................................... 73/112.05
(58) Field of Classification Search ................ 73/112.05
See application file for complete search history.

(56) References Cited

U.S. PATENT DOCUMENTS

| | | | |
|---|---|---|---|
| 5,475,485 A | 12/1995 | Diener | |
| 5,644,394 A | 7/1997 | Owens | |
| 5,670,879 A * | 9/1997 | Zombo et al. | 324/227 |
| 5,781,007 A * | 7/1998 | Partika et al. | 324/220 |
| 5,913,243 A * | 6/1999 | Hopeck et al. | 73/644 |
| 6,082,198 A * | 7/2000 | Sabourin et al. | 73/633 |
| 6,736,011 B2 * | 5/2004 | Zayicek et al. | 73/628 |
| 7,010,982 B2 | 3/2006 | Bergman | |
| 7,032,279 B2 | 4/2006 | McCarvill et al. | |
| 7,174,788 B2 | 2/2007 | Czerw et al. | |
| 7,302,851 B2 | 12/2007 | Czerw et al. | |
| 7,606,445 B2 | 10/2009 | Howard | |
| 7,617,603 B2 * | 11/2009 | Coleman et al. | 29/890.031 |
| 7,654,143 B2 | 2/2010 | Roney et al. | |
| 7,766,726 B2 | 8/2010 | Sherlock et al. | |
| 7,987,721 B2 * | 8/2011 | Schulz et al. | 73/620 |
| 8,028,581 B2 * | 10/2011 | Perkins et al. | 73/622 |
| 2006/0168809 A1 | 8/2006 | McCarvill et al. | |
| 2006/0236769 A1 * | 10/2006 | Tenley et al. | 73/618 |
| 2008/0250860 A1 * | 10/2008 | Clossen-von Lanken Schulz et al. | 73/627 |
| 2011/0178727 A1 * | 7/2011 | Hafenrichter et al. | 702/38 |

* cited by examiner

*Primary Examiner* — Freddie Kirkland, III
(74) *Attorney, Agent, or Firm* — James W. Pemrick; Ernest G. Cusick; Frank A. Landgraff

(57) ABSTRACT

An apparatus is provided for inspecting a component of a turbomachine in-situ. The apparatus includes an end effector having a frame defining a stable platform with a curved surface of the component, a spring loaded suspension attached to the frame, and a probe connected to a wedge member, where the probe and wedge member are connected to the spring loaded suspension. The probe is configured to inspect the component by passing signals through the wedge.

20 Claims, 8 Drawing Sheets

US 8,365,584 B1

APPARATUS FOR INSPECTING TURBOMACHINE COMPONENTS IN-SITU

BACKGROUND OF THE INVENTION

The apparatus described herein relates generally to turbomachines. More specifically, the apparatus relates to inspecting turbomachine components in-situ.

Gas turbine compressor blades can get damaged due to operation. In the event of such damage, timely detection and replacement of these blades are desirable to prevent airfoil liberation and subsequent compressor failure. The current practice for blade inspection requires compressor case removal, which is inevitably time consuming and expensive. The removal of the compressor case for inspection of compressor blades also creates undesirable outage time, thereby resulting in lost income for the machine owner/operator.

BRIEF DESCRIPTION OF THE INVENTION

In an aspect of the present invention, an apparatus is provided for inspecting a component of a turbomachine. The apparatus includes an end effector having a frame defining a stable platform with a curved surface of the component, a spring loaded suspension attached to the frame, and a probe connected to a wedge member, where the probe and wedge member are connected to the spring loaded suspension. The probe is configured to inspect the component in-situ by passing signals through the wedge.

In another aspect of the present invention, an apparatus is provided for inspecting a component of a turbomachine. The apparatus includes an end effector having a frame defining a stable platform with a curved surface of the component, a spring loaded suspension attached to the frame, and an ultrasonic transducer connected to a wedge member. The ultrasonic transducer is capable of sending and receiving ultrasonic signals. The ultrasonic transducer and wedge member are connected to the spring loaded suspension. The wedge member has a rounded bottom configured to fit the curvature of the component and to provide an offset so the signals enter the component at a predetermined angle and distance to an area of interest. An ultrasonic coupling medium supply conduit is connected to the wedge member, and is configured to supply an ultrasonic coupling medium to the wedge member. The ultrasonic transducer is configured to inspect the component by passing signals through the wedge, while the turbomachine component is inspected in-situ.

DETAILED DESCRIPTION OF THE INVENTION

The major challenge in the development of an in-situ blade inspection method and apparatus is to design a mechanism that can deliver the inspection tool to the target blade inside the compressor, due to the stringent spatial constraints imposed by the tight workspace within the compressor flow path. The delivery mechanism should be capable of reaching the desired portions of the target airfoil, blade or vane.

Figure 1:
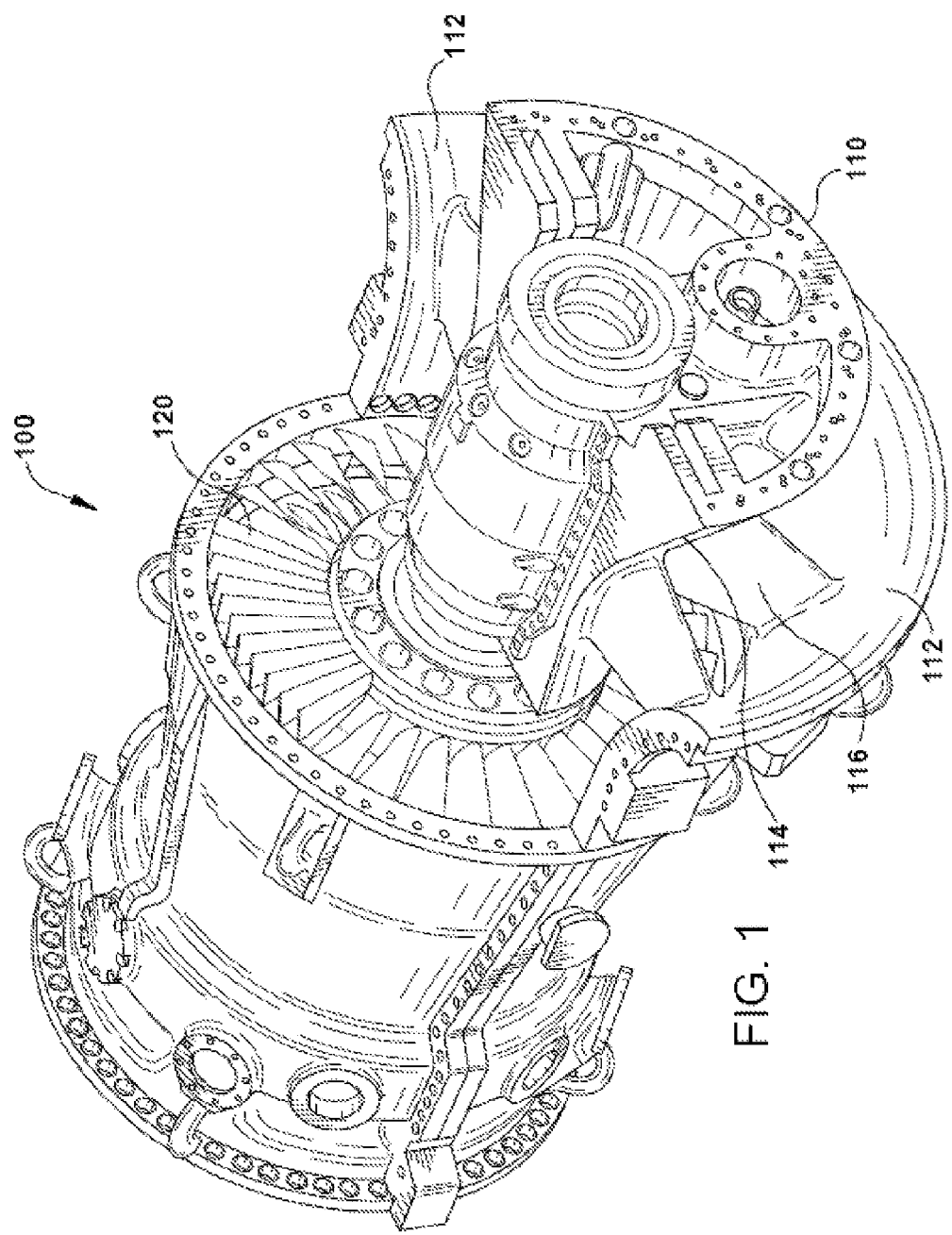
FIG. 1 illustrates a partial, cut-away view of a turbomachine.

FIG. 1 illustrates a partial, cut-away view of a turbomachine 100, which may be a gas turbine compressor. However, it is to be understood that the present invention can be applied to any turbomachine, including but not limited to, gas turbines, steam turbines, compressors, or any machine that transfers energy between a rotor and a fluid. In compressor 100, half of the compressor bell mouth 110 is omitted to show the internal vanes and blades. The bell mouth 110 includes an outer surface 112 and an inner surface 114, and incoming flow passes between these two surfaces. Typically, a plurality of support members 116 are fastened or welded to the outer surface 112 and the inner surface 114 for support. The first stage of stator vanes is called the inlet guide vanes (IGVs) 120.

Figure 2:
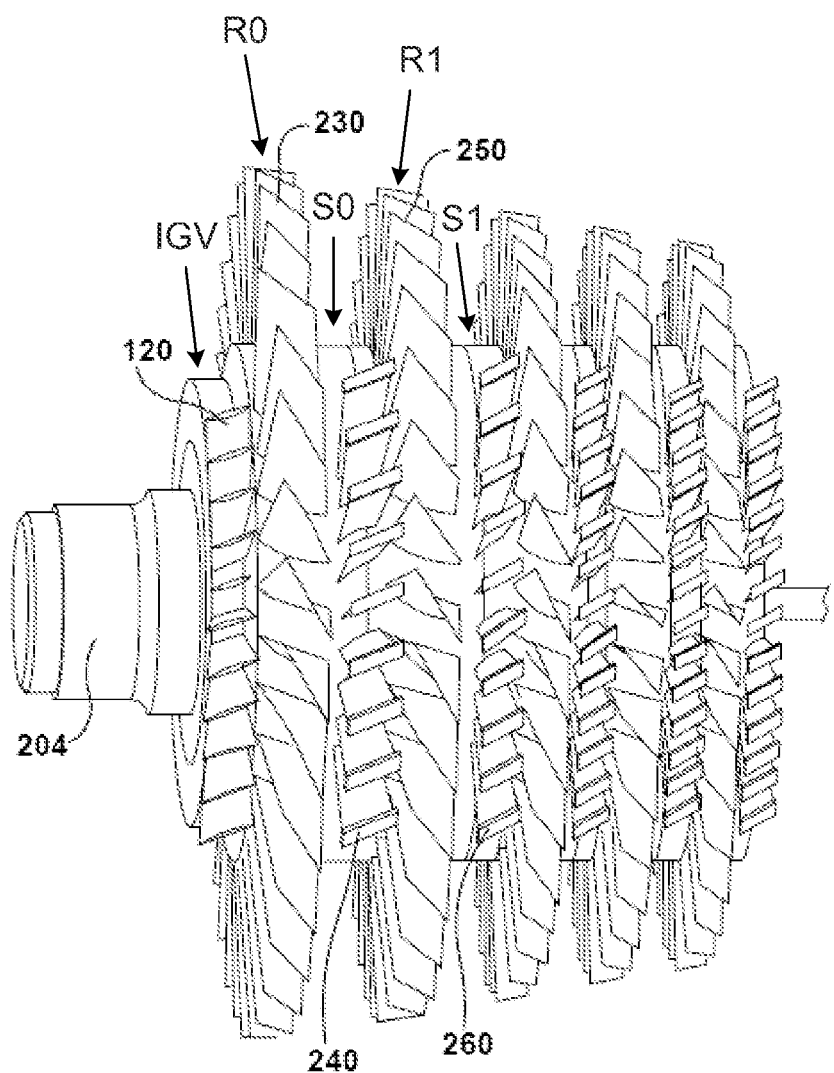
FIG. 2 illustrates a partial perspective view of a compressor showing the airfoils and vanes.

FIG. 2 illustrates a partial perspective view of the compressor airfoils and vanes, with the casing omitted for clarity. The stator vanes are generally fixed, while the rotor airfoils/blades are connected to rotatable rotor 204. The inlet guide vanes 120 are generally fixed as well, but may pitch around a radial axis to vary the direction or amount of incoming flow. The inlet guide vanes 120 are followed by a first row of rotor airfoils 230. The airfoils can also be referred to as the R0 airfoils or R0 blades, as they are part of the R0 stage. The stator vanes 240 are next, and can also be referred to as the S0 vanes, as they are part of the S0 stage. The next row of rotor airfoils/blades 250 can be referred to as the R1 airfoils or R1 blades, as they are part of the R1 stage. The R1 airfoils are followed by the S1 stator vanes 260, as they are part of the S1 stage, and so on.

It would be desirable if a delivery mechanism could go through the bell mouth 110 and reach the target blade or vane, as well as deliver an inspection tool to perform the desired inspection operation. As one example only, an R1 blade can experience various types of damage and this blade could be reached without requiring case removal, according to an aspect of the present invention.

Figure 3:
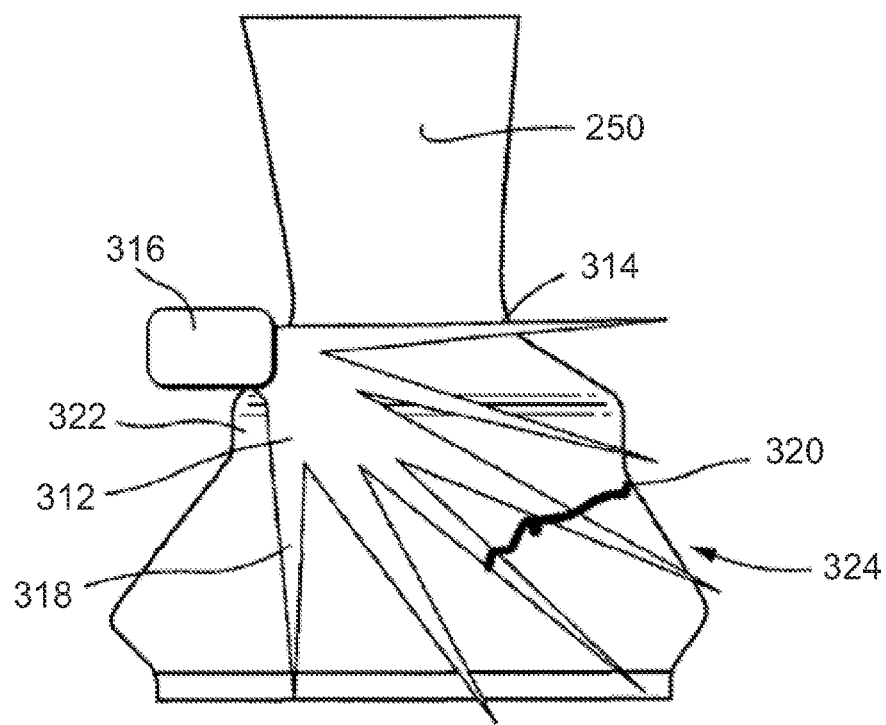
FIG. 3 illustrates a schematic diagram of nondestructively inspecting a component for defects using phased array ultrasound.

Referring to FIG. 3, an aspect of the present invention solves the problem of gaining access to preform nondestructive in-situ testing of machine components, such as an airfoil/blade 250 or vane by scanning, rastering or sweeping an ultrasonic beam 312 (phased array ultrasound) to inspect airfoil 250 for defects using different orientations with one scan. As can be seen in FIG. 3, the horizontal line 314 of beam 312 represents a sound path normal to or directly below a transducer probe 316. The vertical line 318 of beam 312 represents 90 degrees of beam scanning. The cracked line/defect 320 shown in airfoil 250 indicates a defect in the airfoil. As can be seen from FIG. 3, defect 320 can only be seen if the operator using probe 316 is using about a 50° beam angle relative to the normal beam 314. As the surface 322 where transducer 316 is in contact with airfoil 250 changes its orientation, the angle at which beam 312 enters airfoil 250 changes, so that the angle of beam 312 to scan the area of interest 324 in airfoil 250 will change accordingly.

The phased array transducer probe 316 used with the apparatus and method of the present invention may be a linear array probe which is comprised of a series of transducers. Each of these transducers is triggered at predetermined time intervals and receives an ultrasound signal back at predetermined time intervals. This predetermined triggering and receiving is the phasing which allows the steering of beam 312. The ultrasound signals acquired by each transducer are then processed by a computer programmed to give a composite view of the area of interest 324 that is being examined.

To inspect a blade 250 from its blade surface 322, the range of angles which are needed to keep the area of interest 324 in view must first be determined. A sector scan or sweep is then set up which is comprised of the angles required for inspection of the area of interest. During inspection, the entire area of interest 324 can be monitored without interruption of the test. Also, by using an ultrasonic phased array sector scan, parts in a machine with limited access, such as airfoils, can be readily inspected without disassembling the machine containing the airfoil. This is because the inspection method of the present invention does not require complete disassembly of the machine to access all areas of interest by physical means. By using a phased array beam, an operator can see all beam angles of interest in one scan. This allows for a more comprehensive view of the inspection area 324 and reduces the test variation.

Figure 4:
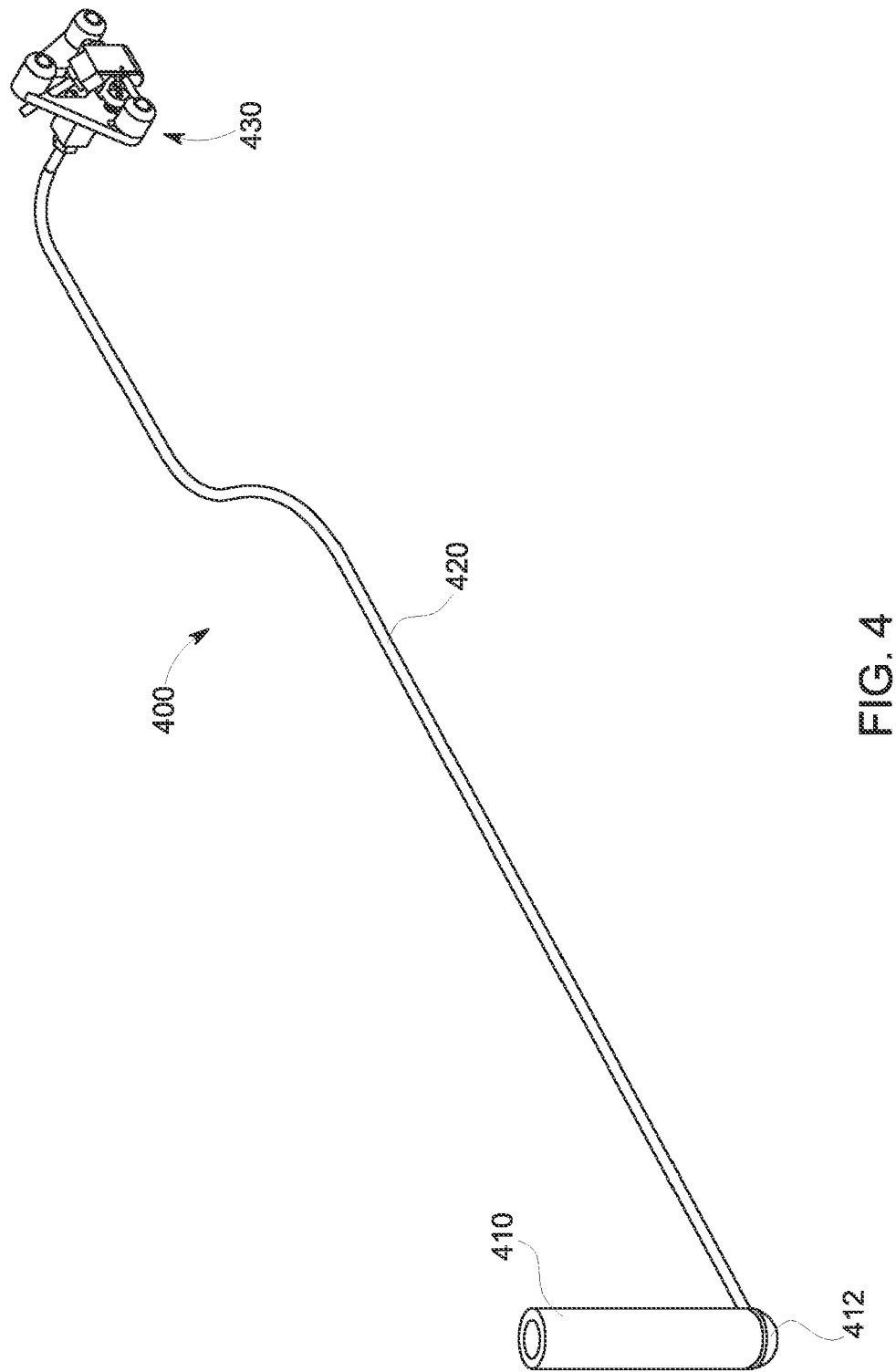
FIG. 4 illustrates a perspective view of an apparatus that can be used to inspect turbomachines in-situ, according to an aspect of the present invention.

FIG. 4 illustrates a perspective view of an apparatus 400 that can be used to inspect turbomachines (e.g., compressors) in-situ, according to an aspect of the present invention. The apparatus 400 includes a handle 410 that is connected to a tube or rod 420. Preferably, the rod (or tube) 420 is at least partially bendable or malleable, so that it may be bent into a suitable or desired shape to fit around (and avoid contact with) the blades and vanes in the compressor stages. The tube 420 is connected to an end effector 430 that contains a transducer probe. The handle 410 may include a rounded bottom 412 into which one end of the tube 420 may be inserted and secured. For example, a set screw (not shown) may pass through the rounded bottom and/or the tube 420 to secure the handle 410 to the tube. The handle 410 is manipulated by an operator to maneuver the apparatus through the various stages of vanes and blades of the compressor.

Figure 5:
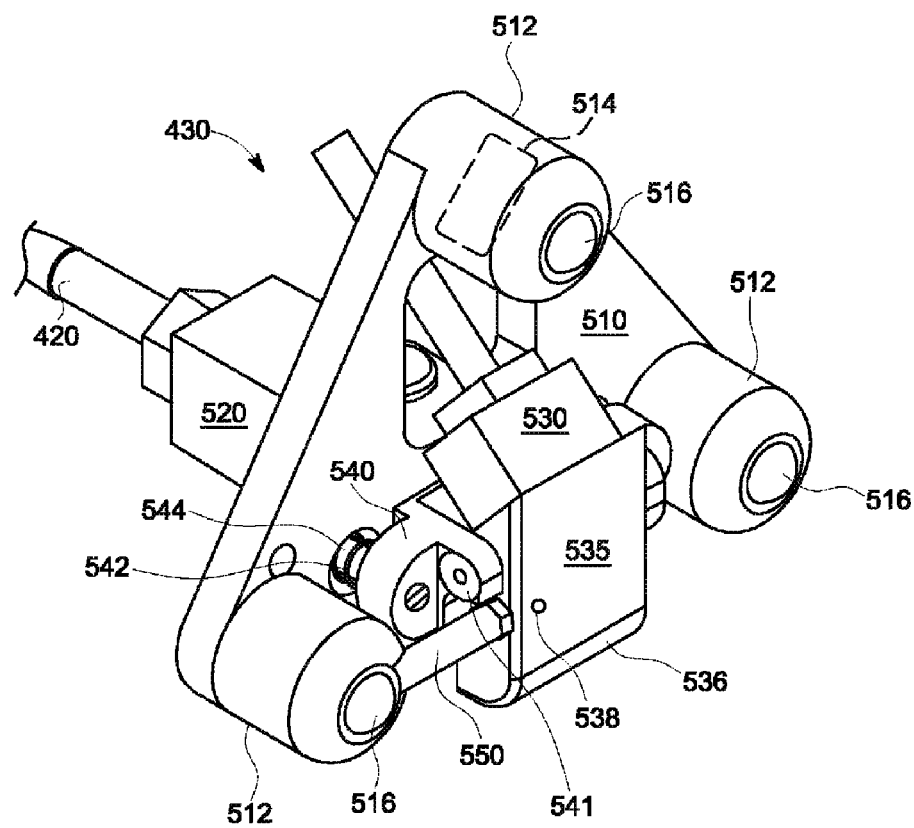
FIG. 5 illustrates a perspective view of the end effector, according to an aspect of the present invention.

FIG. 5 illustrates a perspective view of the end effector 430, according to an aspect of the present invention. The end effector includes a frame 510 that has a substantially triangular shape, and this frame 510 defines a stable platform with a curved surface of the compressor blade or vane. The frame 510 also includes three cylindrical shells 512 that hold magnets 514, and low friction contact points 516 made of a low friction material or including a low friction coating. The magnets 514 (or magnetic elements) provide an attractive force between the end effector 430 and the compressor blade, and this attractive force helps an operator maintain contact between the end effector and blade during an inspection procedure. The low friction coating or low friction material may be formed of polytetrafluoroethylene (PTFE) or any other suitable low friction material that reduces friction and facilitates movement of the end effector 430 along the curved surface of the compressor blade or vane.

The end effector 430 is connected to the rod 420 via a rod coupler 520. One end of the rod 420 may be held in the rod coupler by a compression fitting, a set screw or any other suitable retaining means. The end effector 430 also includes a spring loaded suspension attached to the frame 510. The spring loaded suspension includes the yoke 540, springs 542 and screws 544. The spring loaded suspension provides pitch and roll motion to the probe 530 and wedge member 535 so that it can keep constant and uniform contact with the compressor blade during the scanning of areas or interest for inspection and provides a force to press a yoke 540 toward the blade. The wedge member 535 may be mounted to the yoke 540 via two screws 541 that act as a pivot joint for the wedge member 535. This pivot joint is positioned such that the load from the spring loaded suspension system is directed in line with a region of the wedge member 535 that must be in intimate contact with the blade. This suspension system forces the wedge to be firmly and squarely pressed against the blade even as the frame is slid along the width of the blade and the curvature changes below the wedge member.

The wedge member 535, may be formed of a material that permits transmission of ultrasonic signals, such as poly(methyl methacrylate) (PMMA) or cross-linked polystyrene, and has a rounded bottom 536 to fit the curvature of the blade against the platform and provide a suitable offset to have non-destructive test (NDT) signals (e.g., ultrasonic signals) enter the component or blade at a suitable angle and distance to the areas to be inspected. The wedge member 535 may also be connected to an ultrasonic coupling medium conduit 550 that may be routed back along rod 420 to a source of ultrasonic coupling medium (not shown). The wedge member 535 may have an ultrasonic coupling medium input (not shown) connected to the ultrasonic coupling medium supply conduit 550 and one or more ultrasonic coupling medium outputs 538. The ultrasonic coupling medium is used to couple ultrasonically the airfoil 250 and the wedge 535. Any suitable ultrasonic coupling medium or gel may be used, and as only one non-limiting example, the ultrasonic coupling medium may be a gel comprised of one or more of propylene glycol, glycerin and water.

Figure 6:
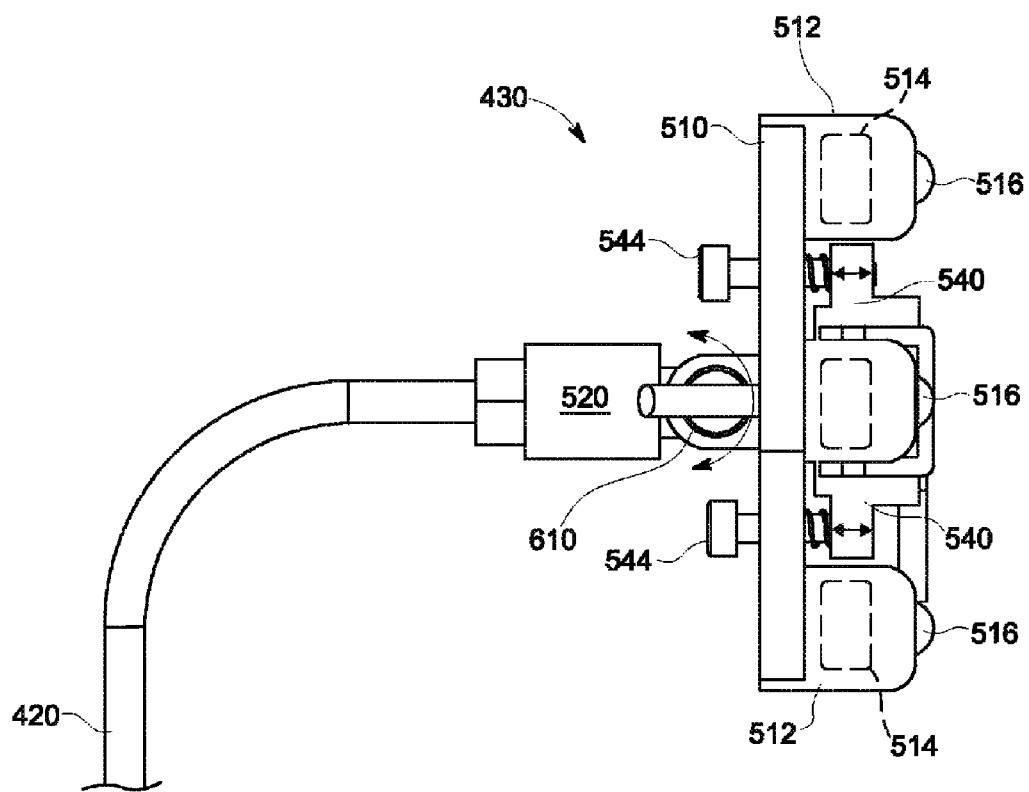
FIG. 6 illustrates a top view of the end effector, according to an aspect of the present invention.

FIG. 6 illustrates a top view of the end effector 430, according to an aspect of the present invention. The end effector 430 is connected to the rod coupler via a pivot joint 610. The pivot joint 610 allows the end effector to pivot up or down in the plane of the drawing (as illustrated by the curved arrow). The spring loaded suspension allows the yoke to move as well. For example, the top of the yoke 540 may move left while the bottom of the yoke 540 may move to the right, in the plane of the drawing.

Figure 7:
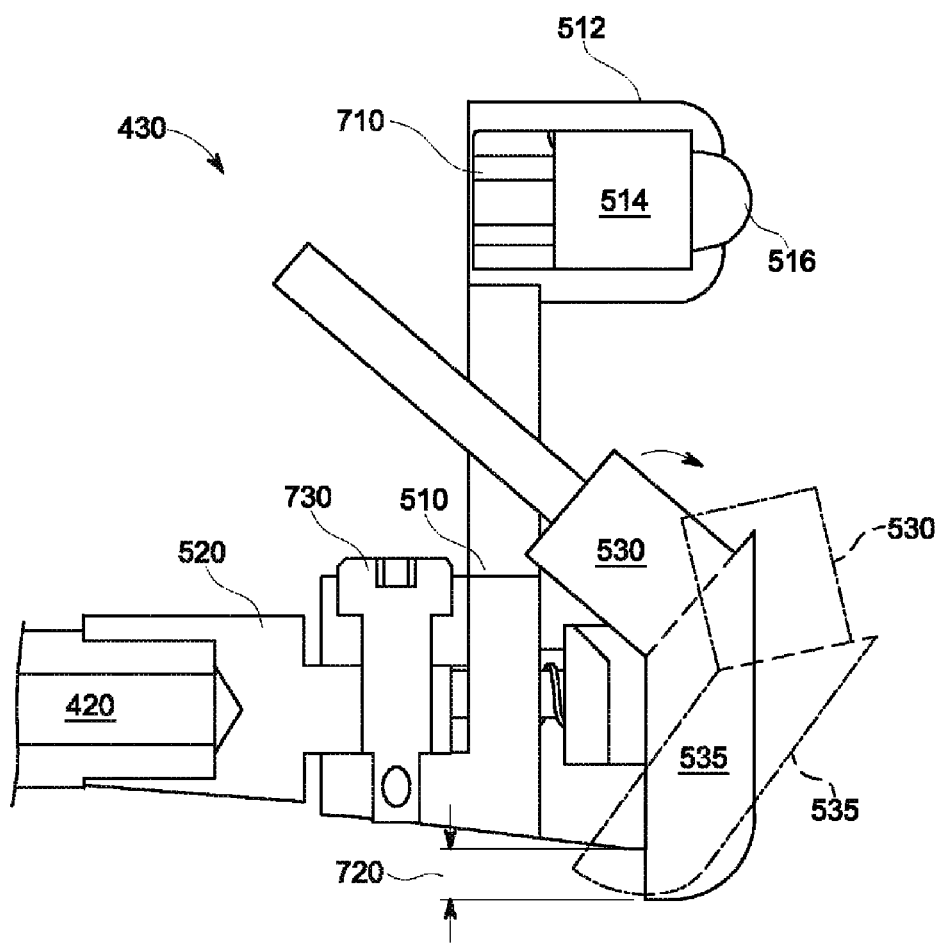
FIG. 7 illustrates a cross-sectional view of the end effector, according to an aspect of the present invention.

FIG. 7 illustrates a cross-sectional view of the end effector 430, according to an aspect of the present invention. The substantially cylindrical shells 512 may have magnets 514 secured by set screws 710. The set screws may 710 also be used to hold the low friction contact points 516 in place as well. The set screws may be externally threaded, and these external threads can mate with internal threads on the interior walls of cylindrical shells 512. The offset distance 720 causes the spring loaded suspension to provide a downward force against the base of the blade and forces the wedge to rotate downward. The pivot joint 610 may be comprised of a shoulder screw 730 that passes through a portion of frame 510 and a tang of rod coupler 520.

Figure 8:
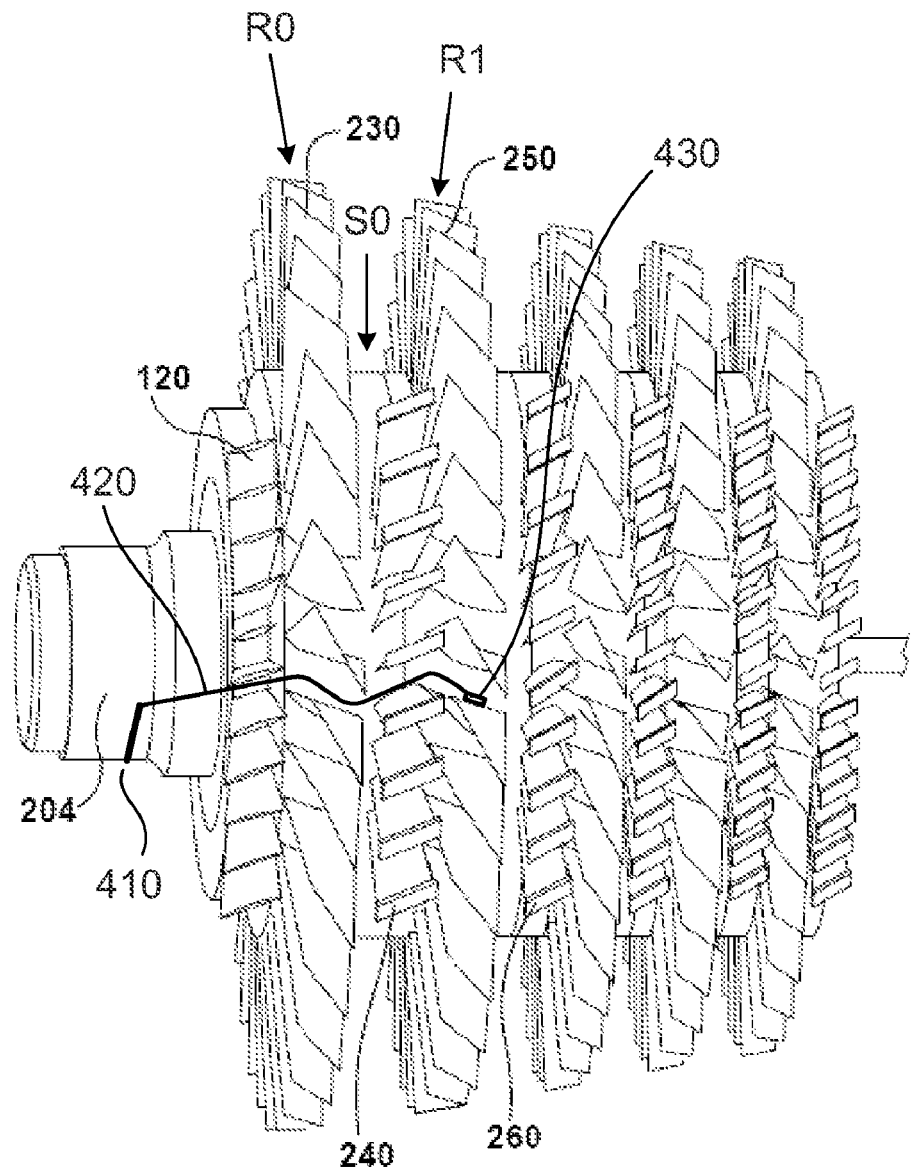
FIG. 8 illustrates a partial perspective view of the compressor airfoils and vanes, with the casing omitted for clarity, and the apparatus inserted to perform an inspection on an R1 rotor blade, according to an aspect of the present invention.

FIG. 8 illustrates a partial perspective view of the compressor airfoils and vanes, with the casing omitted for clarity, and the apparatus 400 inserted to perform an inspection on an R1 rotor blade, according to an aspect of the present invention. The end effector 430 is attached to the bendable rod 420 via the pivot joint 610 and this pivot allows the single degree of freedom necessary to keep the three points (defined by the end of the cylindrical shells/low friction points) in contact with the blade as an operator slides the apparatus 400 back and forth along the base of the blade as the inspection is taking place. The bendable rod 420 allows the operator to maneuver the mechanism into the compressor and place it on the blade with the aid of the magnetic attraction (via magnets 514). The pre-formed shape of rod 420 may be specifically designed so the operator can provide control motions to the end effector 430 to cover all the areas of interest without contacting the various blades/vanes between the operator and the blade being inspected. The bendable rod 420 is maneuvered with the aid of handle 410 with rounded bottom 412 to allow free rotation of the apparatus 400 and end effector 430 as the geometry of the area to be inspected changes along the platform of the blade.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An apparatus adapted for inspecting a component of a turbomachine, the apparatus comprising:
    an end effector comprising:
        a frame defining a stable platform with a curved surface of the component;
        a spring loaded suspension attached to the frame;
        a probe connected to a wedge member, the probe and wedge member connected to the spring loaded suspension;
    wherein the probe is configured to inspect the component in-situ by passing signals through the wedge.

2. The apparatus of claim 1, wherein the probe is an ultrasonic transducer capable of sending and receiving ultrasonic signals.

3. The apparatus of claim 2, the frame further comprising a substantially triangular frame having three substantially cylindrical shells, the substantially cylindrical shells each having a substantially hemispherical contact point for contacting the curved surface of the component.

4. The apparatus of claim 3, each of the three substantially cylindrical shells further comprising:
    a magnetic element; and
    a low friction material located either in or on the substantially hemispherical contact point;
    wherein the magnetic element provides an attractive force to help an operator maintain contact between the end effector and the component, and the low friction material facilitates movement of the end effector along the curved surface of the component.

5. The apparatus of claim 4, wherein the low friction material is polytetrafluoroethylene (PTFE).

6. The apparatus of claim 2, further comprising:
    a bendable rod connected to the end effector;
    a handle attached to the bendable rod; and
    wherein the frame is connected to the bendable rod via a pivoting connection and a rod coupler.

7. The apparatus of claim 2, the end effector further comprising:
    a yoke connected to the spring loaded suspension and the probe and wedge member, the yoke connected to the wedge member by a pivoting connection.

8. The apparatus of claim 2, the wedge member further comprising:
    a rounded bottom configured to fit the curvature of the component and to provide an offset so the signals enter the component at a predetermined angle and distance to an area of interest.

9. The apparatus of claim 2, the end effector further comprising:
    an ultrasonic coupling medium supply conduit connected to the wedge member;
    wherein the ultrasonic coupling medium supply conduit supplies an ultrasonic coupling medium, and the wedge member comprises an ultrasonic coupling medium input connected to the ultrasonic coupling medium supply conduit and an ultrasonic coupling medium output to facilitate ultrasonic coupling between the wedge member and the component.

10. The apparatus of claim 9, wherein the ultrasonic coupling medium is a gel comprising at least one of, propylene glycol, glycerin and water.

11. The apparatus of claim 2, wherein the turbomachine is at least one of a compressor and a gas turbine.

12. The apparatus of claim 11, wherein the turbomachine is the compressor and the component is at least one of a blade and a vane.

13. An apparatus adapted for inspecting a component of a turbomachine, the apparatus comprising:
    an end effector comprising:
        a frame defining a stable platform with a curved surface of the component;
        a spring loaded suspension attached to the frame;
        an ultrasonic transducer connected to a wedge member, the ultrasonic transducer capable of sending and receiving ultrasonic signals, the ultrasonic transducer and wedge member connected to the spring loaded suspension, the wedge member having a rounded bottom configured to fit the curvature of the component and to provide an offset so the signals enter the component at a predetermined angle and distance to an area of interest;
        an ultrasonic coupling medium supply conduit connected to the wedge member, the ultrasonic coupling medium supply conduit configured to supply an ultrasonic coupling medium to the wedge member; and
    wherein the ultrasonic transducer is configured to inspect the component by passing signals through the wedge, while the component is inspected in-situ.

14. The apparatus of claim 13, wherein the wedge member comprises an ultrasonic coupling medium input connected to the ultrasonic coupling medium supply conduit and an ultrasonic coupling medium output to direct the ultrasonic coupling medium to a location between the wedge member and the component.

15. The apparatus of claim 13, the frame further comprising a substantially triangular frame having three substantially cylindrical shells, the substantially cylindrical shells each having a substantially hemispherical contact point for contacting the curved surface of the component.

16. The apparatus of claim 15, each of the three substantially cylindrical shells further comprising:
    a magnetic element; and
    a low friction material located either in or on the substantially hemispherical contact point;
    wherein the magnetic element provides an attractive force to help an operator maintain contact between the end effector and the component, and the low friction material facilitates movement of the end effector along the curved surface of the component.

17. The apparatus of claim 13, further comprising:
a bendable rod connected to the end effector;
a handle attached to the bendable rod; and
wherein the frame is connected to the bendable rod via a pivoting connection and a rod coupler.

18. The apparatus of claim 13, the end effector further comprising:
a yoke connected to the spring loaded suspension and the probe and wedge member, the yoke connected to the wedge member by a pivoting connection.

19. The apparatus of claim 13, wherein the turbomachine is at least one of a compressor and a gas turbine.

20. The apparatus of claim 19, wherein the turbomachine is the compressor and the component is at least one of a blade and a vane.

* * * * *